(12) United States Patent
Cowe et al.

(10) Patent No.: US 11,253,651 B2
(45) Date of Patent: Feb. 22, 2022

(54) MEDICAMENT DELIVERY DEVICE

(71) Applicant: Owen Mumford Limited, Oxford (GB)

(72) Inventors: Toby Cowe, Oxfordshire (GB); Colin Webb, Oxfordshire (GB)

(73) Assignee: Owen Mumford Limited, Oxford (GB)

( * ) Notice: Subject to any disclaimer, the term of this patent is extended or adjusted under 35 U.S.C. 154(b) by 213 days.

(21) Appl. No.: 16/461,504

(22) PCT Filed: Nov. 17, 2017

(86) PCT No.: PCT/GB2017/053468
§ 371 (c)(1),
(2) Date: May 16, 2019

(87) PCT Pub. No.: WO2018/091915
PCT Pub. Date: May 24, 2018

(65) Prior Publication Data
US 2019/0328974 A1    Oct. 31, 2019

(30) Foreign Application Priority Data
Nov. 18, 2016    (GB) ...................................... 1619556

(51) Int. Cl.
*A61M 5/24*    (2006.01)
*A61M 5/20*    (2006.01)
(Continued)

(52) U.S. Cl.
CPC ........ *A61M 5/2448* (2013.01); *A61M 5/2066* (2013.01); *A61M 5/2429* (2013.01);
(Continued)

(58) Field of Classification Search
CPC .............. A61M 5/2448; A61M 5/2066; A61M 5/2033; A61M 5/2429; A61M 5/31596;
(Continued)

(56) References Cited

U.S. PATENT DOCUMENTS 2,591,706 A    4/1952 Lockhart
3,680,558 A    8/1972 Kapelowitz
(Continued)

OTHER PUBLICATIONS

Feb. 26, 2018 Transmittal of ISR and Written Opinion of Int'l Searching Authority for PCT/GB2017/053468.

*Primary Examiner* — Laura A Bouchelle
*Assistant Examiner* — Luke J. Efta
(74) *Attorney, Agent, or Firm* — Quarles & Brady LLP

(57) ABSTRACT

A medicament delivery device (100) for delivery of medicament through a cannula (132) from a cartridge (10), the device comprising a first container (11) for storage of a first substance, a second container (12), and valve means for closing a distal end of the second chamber (12), the second container (12) being arranged coaxially with respect to the first container (11), a mixing element (304) being provided for causing displacement of the second substance into the first container (11) through the valve means in a mixing stroke, a release element being provided for holding the mixing element (304) in an initial position and being operable to release the mixing element (304) to initiate the mixing stroke, there being a needle shroud (400) for shrouding the cannula, and removal of the needle shroud (400) from the cannula (132) causing operation of the release element.

25 Claims, 17 Drawing Sheets

(51) Int. Cl.
*A61M 5/315* (2006.01)
*A61M 5/32* (2006.01)
*A61M 5/19* (2006.01)
*A61M 5/28* (2006.01)

(52) U.S. Cl.
CPC ...... *A61M 5/31596* (2013.01); *A61M 5/3202* (2013.01); *A61M 5/19* (2013.01); *A61M 5/284* (2013.01); *A61M 5/285* (2013.01); *A61M 2005/247* (2013.01)

(58) Field of Classification Search
CPC ...... A61M 5/3202; A61M 5/19; A61M 5/284; A61M 5/285; A61M 2005/247
See application file for complete search history.

(56) References Cited

U.S. PATENT DOCUMENTS

2002/0042592 A1* 4/2002 Wilmot ................ A61M 5/343
604/92
2016/0220764 A1* 8/2016 Durvasula ........... A61M 5/2033
2016/0263320 A1 9/2016 Constantineau et al.
2020/0155761 A1* 5/2020 Holmqvist ........... A61J 1/2013

\* cited by examiner

MEDICAMENT DELIVERY DEVICE

The present application is a § 371 submission of international application no. PCT/GB2017/053468, filed 17 Nov. 2017 and titled Medicament Delivery Device, which was published in the English language on 24 May 2018 with publication no. WO 2018/091915 A1, and which claims the benefit of the filing date of GB 16 19556.2 filed 18 Nov. 2016, the contents of which are incorporated herein by reference.

This invention relates to devices suitable for delivering medicament substances to a patient. In particular, but not exclusively, the invention relates to a disposable medicament delivery device for use with cartridge-type primary packaging containing constituents of a reconstitutable medicament. This invention further relates to medicaments, including pharmaceutical compositions, for subcutaneous injection or infusion disposed within the delivery devices and methods of treating patients with conditions susceptible to treatment by delivering the medicament using the delivery devices described herein.

Medicaments for subcutaneous injection or infusion are used in therapy in various different clinical situations. In some cases, it is necessary or advantageous to supply a medicament to a user as two separate components, and to mix the components just prior to use.

For instance, some injectable medicaments, such as blood factors for the treatment of haemophilia and glucagon for the treatment of severe hypoglycaemia, have an unacceptably short shelf-life when in liquid form, and are therefore most commonly supplied in freeze-dried or lyophilised form as a solid powder. In the lyophilised form, the shelf life of the medicament is substantially extended. Prior to use, the medicament must be reconstituted by mixing with a suitable sterile diluent, such as water or saline.

In a conventional arrangement, the solid component of a medicament is supplied in a vial, and the liquid diluent is supplied in a separate syringe. The vial is typically closed with a polymeric membrane or septum that can be pierced by a needle of the syringe. In use, the syringe needle is inserted through the septum, and the diluent is injected into the vial to mix with the solid component. The vial is then shaken to encourage thorough mixing. The syringe may be removed from the vial during shaking, and so the septum is typically self-sealing to prevent leakage of the vial contents once the needle is withdrawn.

After reconstitution of the medicament, the syringe is re-inserted in the vial if necessary and then the mixture is drawn into the syringe. The syringe, now containing the reconstituted medicament, is removed from the vial and can be used to administer the reconstituted medicament to a patient by injection.

This conventional arrangement has several disadvantages. The need to provide a separate vial and syringe, and to keep those components sterile, can be inconvenient. Also, the number of steps involved and the relatively complex actions required can make the arrangement unattractive in some clinical situations, such as self-administration by a patient at home. Self-administration can be particularly difficult for young patients, or those with reduced manual dexterity.

In the field of single-component, non-reconstitutable liquid medicaments, the problem of providing medicaments in a more convenient form for injection has been addressed by the development of several different types of medicament delivery device.

For example, the need for a separate vial and syringe can be avoided by the use of pre-filled, disposable syringes containing a single dose of the medicament. In one common pre-filled syringe design, sold under the registered trade mark Hypak (Becton Dickinson, N.J., USA), a needle is permanently fixed to the distal end of the syringe body, and the needle is kept sterile by a removable cap. In other examples, a pre-filled syringe body is provided with a suitable connection for a needle, such as a Luer connector.

More sophisticated auto-injector devices designed for self-administration of a single, fixed dose of non-reconstitutable medicament are also known. Typically, in such devices, one or more of needle insertion, medicament delivery, dose indication, needle retraction and deployment of a needle shield after injection are triggered by one or more user operations, such as operating a trigger button or slider. The medicament dose in an auto-injector device may be provided in the form of a disposable, pre-filled glass syringe with a fixed needle, such as a Hypak syringe of the type described above, or in a cartridge or other package.

Other known single-component medicament delivery devices include safety syringes, injection pens, infusion pumps and so on. In these cases, the medicament may be contained in cartridges or other packages that are specifically designed for the device.

In contrast, relatively few devices suitable for the delivery of reconstitutable medicaments are available. Moreover, those devices that are available typically require a number of different user operations in order to actuate the mixing, insertion, and injection steps. This increases the complexity for users, and thereby raises the potential for mis-operation.

Accordingly, it is an object of the invention to provide a medicament delivery device that is suitable for a reconstitutable medicament and that allows for simple user operation. A further object of the invention is to provide medicaments, including pharmaceutical compositions, for subcutaneous injection or infusion disposed within the delivery devices and methods of treating patients with conditions susceptible to treatment by delivering the medicament using the delivery devices described herein.

Against this background, and from one aspect, the present invention resides in a medicament delivery device for delivery of medicament through a cannula from a cartridge comprising a first container for storage of a first substance, a second container for storage of a second substance and being arranged coaxially with respect to the first container, and valve means for closing a distal end of the second chamber, the medicament delivery device comprising: a mixing element for causing the displacement of the second substance into the first container through the valve means in a mixing stroke; a release element for holding the mixing element in an initial position and operable to release the mixing element to initiate the mixing stroke; and a needle shroud for shrouding the cannula, wherein removal of the needle shroud from the cannula causes operation of the release element.

In this way, the medicament delivery device allows for greatly simplified user operation for the delivery of reconstitutable medicaments. That is, the medicament-mixing operation required to reconstitute the medicament is automatically initiated by the user's removal of the needle shroud. Consequently, there is a reduced risk of mis-operation of the device. A mechanical coupling or linkage may used to connect between the needle shroud and the release element to hold it in its initial position, and the removal of the needle shroud disconnects the coupling or linkage to operate the release element. In other arrangements, the release element may itself be held in a locking position by the needle shroud and the removal of the needle shroud acts to operate the release element. Medicaments, including pharmaceutical compositions, contemplated for use in the delivery device may comprise small molecules, vaccines, live or attenuated cells, oligonucleotides, DNA, peptides, antibodies, and recombinant or naturally occurring proteins, whether human or animal, useful for prophylactic, therapeutic or diagnostic application. The active ingredient can be natural, synthetic, semi-synthetic or derivatives thereof. A wide range of active ingredients are contemplated. These include, for example, hormones, cytokines, hematopoietic factors, growth factors, antiobesity factors, trophic factors, anti-inflammatory factors, and enzymes. The pharmaceutical compositions also may include, but are not limited to, insulin, gastrin, prolactin, human growth hormone (hGH), adrenocorticotropic hormone (ACTH), thyroid stimulating hormone (TSH), luteinizing hormone (LH), follicle stimulating hormone (FSH), human parathyroid hormone (PTH), glucagon, glucagons-like peptide 1 (GLP-1), glucagons-like peptide 2 (GLP-2), insulin-like growth factors (IGFs) such as insulin growth factor I (IGF I), insulin growth factor II (IGF II), growth hormone-releasing factor (GRF), human chorionic gonadotropin (HCG), gonadotropin-releasing hormone, motilin, interferons (alpha, beta, gamma), interleukins (e.g., IL-1, IL-2, IL-4, IL-5, IL-6, IL-9, IL-11, IL-12, IL-13, IL-15, IL-16, IL-17, IL-18, IL-20 or IL-21), interleukin-1 receptor antagonists (IL-lra), tumor necrosis factor (TNF), tumor necrosis factor-binding protein (TNF-bp), CD40L, CD30L, erythropoietin (EPO), plasminogen activator inhibitor 1, plasminogen activator inhibitor 2, von Willebrandt factor, thrombopoietin, angiopoietin, granulocyte-colony stimulating factor (G-CSF), stem cell factor (SCF), leptin (OB protein), brain derived neurotrophic factor (BDNF), glial derived neurotrophic factor (GDNF), neurotrophic factor 3 (NT3), fibroblast growth factors (FGF), neurotrophic growth factor (NGF), bone growth factors such as osteoprotegerin (OPG), transforming growth factors, epidermal growth factor (EGF), vascular endothelial growth factor (VEGF), macrophage colony stimulating factor (M-CSF), granulocyte macrophage colony stimulating factor (GM-CSF), megakaryocyte derived growth factor (MGDF), keratinocyte growth factor (KGF), platelet-derived growth factor (PGDF), novel erythropoiesis stimulating protein (NESP), bone morphogenetic protein (BMP), superoxide dismutase (SOD), tissue plasminogen activator (TPA), pro-urokinase, urokinase, streptokinase, kallikrein, a protease inhibitor e.g. aprotinin, an enzyme such as asparaginase, arginase, arginine deaminase, adenosine deaminase, ribonuclease, catalase, uricase, bilirubin oxidase, trypsin, papain, alkaline phosphatase, glucoronidase, purine nucleoside phosphorylase or batroxobin, an opioid, e.g. endorphins, enkephalins or non-natural opioids, a neuropeptide, neuropeptide Y, calcitonin, cholecystokinins, corticotrophin-releasing factor, vasopressin, oxytocin, antidiuretic hormones, thyrotropin releasing hormone, relaxin, peptideYY, pancreastic polypeptide, CART (cocaine and amphetamine regulated transcript), a CART related peptide, perilipin, melanocortins (melanocyte-stimulating hormones) such as MSH, melanin-concentrating hormones, natriuretic peptides, adrenomedullin, endothelin, secretin, amylin, vasoactive intestinal peptide (VIP), pituary adenylate cyclase activating polypeptide (PACAP), bombesin, bombesin-like peptides, thymosin, heparin-binding protein, soluble CD4, hypothalmic releasing factor, melanotonins, and human antibodies and humanized antibodies, and other pharmaceutical compositions suitable for administration with the delivery devices. The term proteins, as used herein, includes peptides, polypeptides, consensus molecules, analogs, derivatives or combinations thereof.

The pharmaceutical compositions also may include therapeutic and pharmaceutic agents such as, but not limited to: antiproliferative/antimitotic agents including natural products such as vinca alkaloids (i.e. vinblastine, vincristine, and vinorelbine), paclitaxel, epipidopodophyllotoxins (i.e. etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which don't have the capacity to synthesize their own asparagine); antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nirtosoureas (carmustine (BCNU) and analogs, streptozocin), trazenes-dacarbazinine (DTIC); antiproliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine{cladribine}); platinum coordination complexes (cisplatin, carboplatin), procarbazine, hydroxyurea, mitotane, aminoglutethimide; hormones (i.e. estrogen); Anticoaglants (heparin, synthetic heparin salts and other inhibitors of thrombin); fibrinolytic agents (such as tissue plasminogen activator, streptokinase and urokinase); antiplatelet (aspirin, dipyridamole, ticlopidine, clopidogrel, abciximab); antimigratory; antisecretory (breveldin); antiinflammatory: such as adrenocortical steroids (cortisol, cortisone, fludrocortisone, prednisone, prednisolone, 6a-methylprednisolone, triamcinolone, betamethasone, and dexamethasone), non-steroidal agents (salicylic acid derivatives i.e. aspirin; para-aminophenol derivatives i.e. acetominophen; Indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressive: (cyclosporine, tacrolimus (FK-506), sirolimus (rapamycin), azathioprine, mycophenolate mofetil); nitric oxide donors; anti-sense olgio nucleotides and combinations thereof.

The pharmaceutical compositions include any extended half-life variants of active ingredients contained therein or analogues thereof. Thus, the active ingredients can be any long acting variants of the active ingredient listed herein or analogues thereof. In some embodiments, the active ingredient includes any extended half-life or long acting variants of hGH, insulin, glucagon, glucagons-like peptide 1 (GLP-1), glucagons-like peptide 2 (GLP-2), insulin-like growth factors (IGFs). In some embodiments, the active ingredient is an extended half-life or long acting variant of hGH. Examples of extended half-life or long acting variants of hGH include, but are not limited to LB03002, NNC126-0883, NNC0195-0092, MOD-4023, ACP-001, Albutropin, somavaratan (VRS-317), and profuse GH.

In embodiments, the mixing element comprises a spring. As such, for example, the mixing element may itself be a spring which acts to move one of the containers relative to the other for mixing the substances by creating a pressure differential between their chambers.

In embodiments, the first container is moved in the distal direction with respect to the second container in the mixing stroke for displacing the second substance into the first container. In this way, the movement causes the volume of the first chamber of the first container to be increased, resulting in a relative drop in pressure that draws the second substance into the first container.

In embodiments, the medicament delivery device may further comprise a housing for receiving the cartridge, and wherein the second container is restrained relative to the housing during the mixing stroke. In this way, the second container may be held in place while the first container is moved in the distal direction away from it during the mixing stroke. The second container may be released from its attachment relative to the housing to initiate the drive stroke.

In embodiments, the first container is biased in the distal direction by the mixing element and the release element restrains the first container in an initial position against the distal bias. In this way, the release element may lock the first container in a position towards the proximal end of the device and, once operated, may release the first container to allow it move distally from this proximal starting position. The first container may be supported by a moveable carriage, with the release element engaging with carriage to restrain the first container. The carriage and release element may comprise corresponding track and follower formations which, when aligned, allow the carriage and first container to move distally. In embodiments, the release element is rotated on removal of the needle shroud for aligning the track and follower formations of carriage and release element. This rotation may be actuated, for example, by a spring bias acting on the release element or by engagement of cam formations on the carriage and/or the release element. For example, in embodiments, the mixing spring may apply a distal biasing force to the carriage, which may be translated to a rotational bias in the release element by the cam formations. While the needle shroud is still engaged with the release element, it may restrain its rotation against this bias for preventing the release of the carriage.

In alternative embodiments, the mixing element comprises a stopper for being driven by a mixing spring in the mixing stroke. As such, the device may comprise a mixing spring for driving the mixing element in the mixing stroke. In this way, a spring, such as a compression spring, may apply an axial drive force for moving the mixing element through the mixing stroke.

In embodiments, the mixing element comprises a latch formation for engagement with the release element when in the initial position. In this way, the mixing element is fastened to the release element by a mechanical lock to restrain its movement.

In embodiments, the release element is moveable relative to the latch formation for releasing the mixing element. In this way, a simple lock and release mechanism may be provided by moving the release element within the device.

In embodiments, operation of the release element comprises rotational movement for aligning a slot provided in the release element with the latch formation to release the mixing element. In this way, the mixing element is mechanically locked to the release element when the release element is in an initial rotational orientation. The rotation of the release element to an aligned rotational orientation then removes the engagement between the release element and the latch formation, thereby disengaging the mechanical lock between the elements to release the mixing element. Alternative embodiments are also envisaged. For example, the device may comprise a container shroud that extends longitudinally around at least a portion of the body of the device and is removable with the needle shroud from the device's the front end. Removal of the container shroud can in turn remove a restraining pin that holds the mixing element in its initial position. As such, in use, removal of the needle shroud removes the container shroud, which removes the restraining pin to initiate mixing. The mixing pin may be flexible to facilitate its removal from its latching position. It will also be understood that the container shroud and needle shroud may be formed integrally.

In embodiments, the medicament delivery device further comprises a housing for receiving the cartridge and a chassis rotatable within the housing to initiate the mixing stroke upon removal of the needle shroud from the cannula. In this way, the chassis may provide a mechanical coupling or linkage between the needle shroud and the release element. The needle shroud may provide a rotational lock between the chassis and the housing and, in turn, the chassis can provide a coupling to rotationally lock the release element in its initial position holding the mixing element. As such, the chassis is held in a locked state in the initial position, and removal of the needle shroud transitions the chassis to an unlocked state for permitting movement of the release element to release the mixing element. The mixing stroke is therefore initiated by the removal of the needle shroud that acts to release the coupling that rotationally locks the release element to the housing.

In embodiments, the housing comprises a keying formation for engagement with the mixing element to rotationally lock the mixing element relative to the housing when in its initial position. In this way, the mixing element may be rotationally held in place when the release element is moved relative to it until the mixing stroke is initiated.

In embodiments, the chassis comprises a chassis body and a control sleeve rotationally locked to the chassis body and axially moveable relative thereto. In this way, the chassis body and a control sleeve are coupled and forming a linkage that allows the axial length of the chassis to reduce during the delivery stroke of the device. As such, components that move axially during the delivery stroke can be fixably mounted to the chassis.

In embodiments, the needle shroud engages with the housing and the chassis when shrouding the cannula for preventing relative rotation therebetween. In this way, removal of the needle shroud releases the coupling, rotationally locking the housing and the release element, to initiate the mixing stroke.

In embodiments, the needle shroud comprises keying formations for engagement with the housing and the chassis for preventing relative rotation. In this way, the keying formations can key into corresponding formations provided in the housing and the chassis to rotationally lock these components when the needle shroud is shrouding the cannula.

In embodiments, the chassis is rotationally locked to the release element. In this way, the chassis is directly connected to the release element for coupling between the needle shroud and the release element. Consequently, release of the chassis to its unlocked state by the removal of the needle shroud allows the release element to rotate within the housing.

In embodiments, the release element is biased for rotation to release the mixing element. In this way, the release element may be held in its initial position by restraining its rotation, and removal of the restraint thereby allows the release element to rotate under its rotational bias for initiating the mixing stroke.

In embodiments, the latch formation engages with the release element at a cam surface for biasing the release element to rotate to release the mixing element. In this way, an axial force acting between the latch formation and the release element, such as that provided by a compression spring, may be translated to a rotational bias.

In embodiments, the bias of the mixing spring on the mixing element in the distal direction applies the rotational bias to the release element through the cam surface. In this way, the spring used to drive the mixing element through the mixing stroke may also be used to provide the bias for initiating the release of the mixing element.

In embodiments, the needle shroud comprises a cap projecting from the distal end of the device for facilitating removal of the needle shroud by a user. In this way, even if the body of the needle shroud is disposed within the housing, the cap allows the user to easily de-shield the cannula.

In embodiments, the release element is further moveable in the distal direction to cause movement of the second container in the distal direction for displacing a mixture of the first and second substances through the cannula in a delivery stroke of the device. In this way, the release element may also function as a drive element for driving the delivery stroke of the device. As such, an auto-injector operation may be provided for the delivery of the reconstituted medicament. In this respect, the release element may be axially locked within the housing by latches and the device may comprise a button operable to disengage the latches for releasing the release element. A drive spring may be provided for moving the release element in the distal direction when released.

In embodiments, the medicament delivery device may further comprise a needle assembly supporting the cannula, the needle assembly comprising a sealing ring for forming a sterile seal around a coupling between the first container and a proximal end of the cannula. The needle shroud may also comprise a sealing element for forming a sterile seal around a distal end of the cannula.

According to a further aspect of the present invention, there is provided a combination of a device according to the above statements and a cartridge.

Another aspect of this invention is directed to one or more of the medicaments, including one or more pharmaceutical compositions, as described above for subcutaneous injection or infusion, disposed within the medicament delivery devices described herein for the delivery of the medicament. Additionally, this invention contemplates methods of administering one or more of the medicaments, including pharmaceutical compositions, to patients with conditions susceptible to treatment with the medicaments, as well as methods of treating those conditions, by delivering the appropriate medicament using the delivery devices described herein.

Preferred and/or optional features of each embodiment and aspect of the invention may also be used alone or in appropriate combinations not explicitly described herein Embodiments of the present invention will now be described, by way of example only, with reference to the accompanying drawings, in which like reference numerals are used for like features, and in which.

Figure 14A:
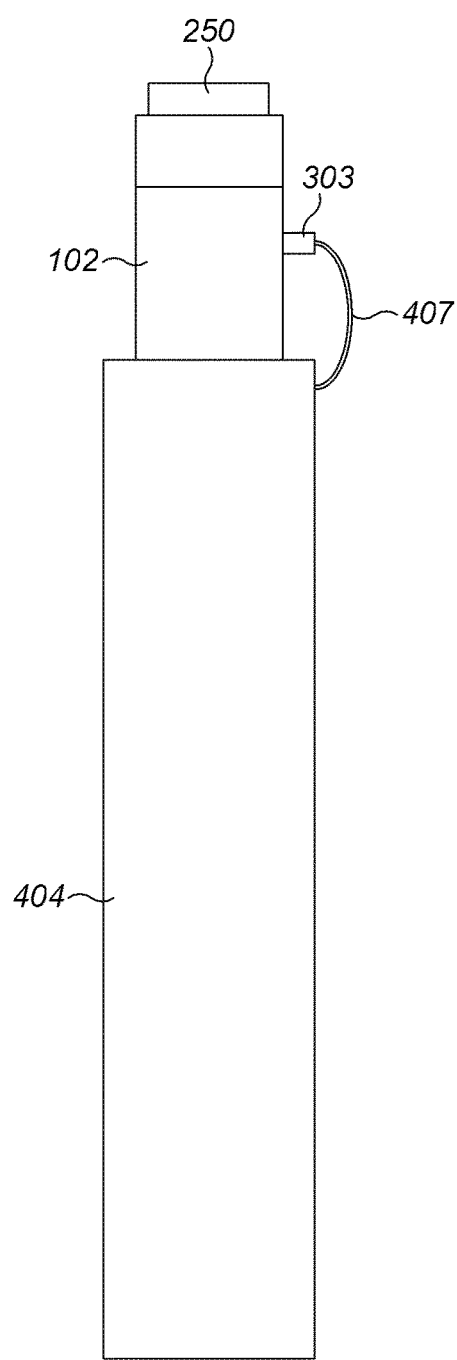
Figure 14B:
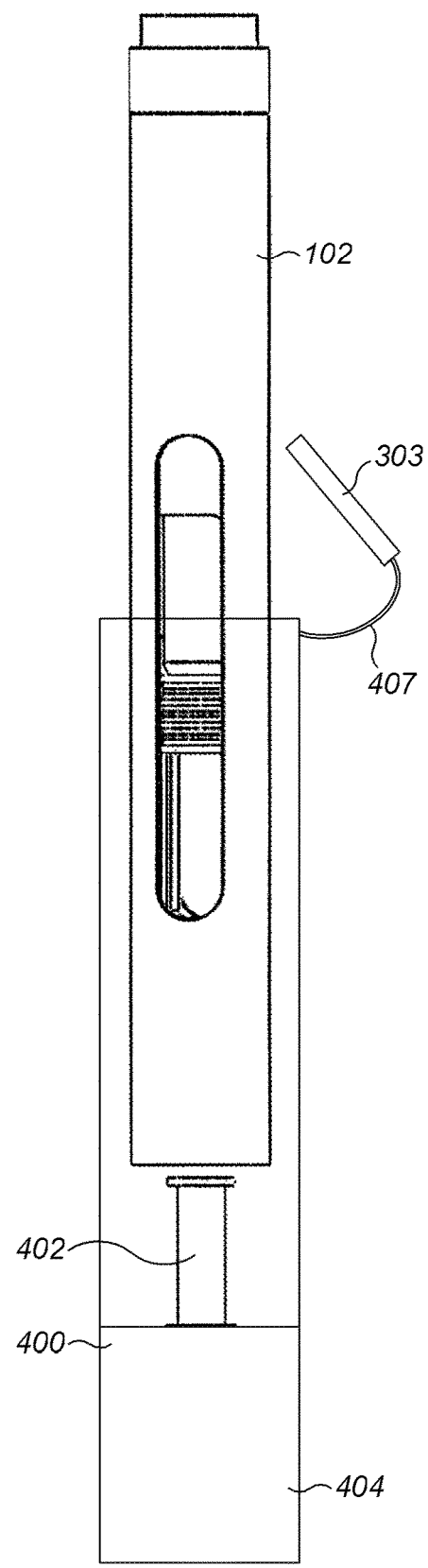
Figure 15A:
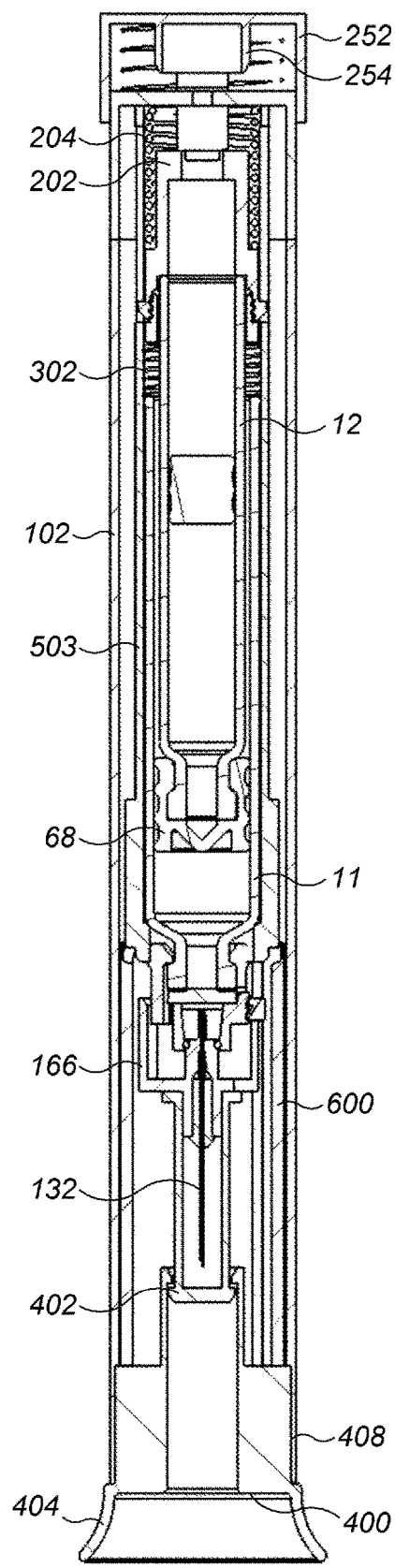
Figure 15B:
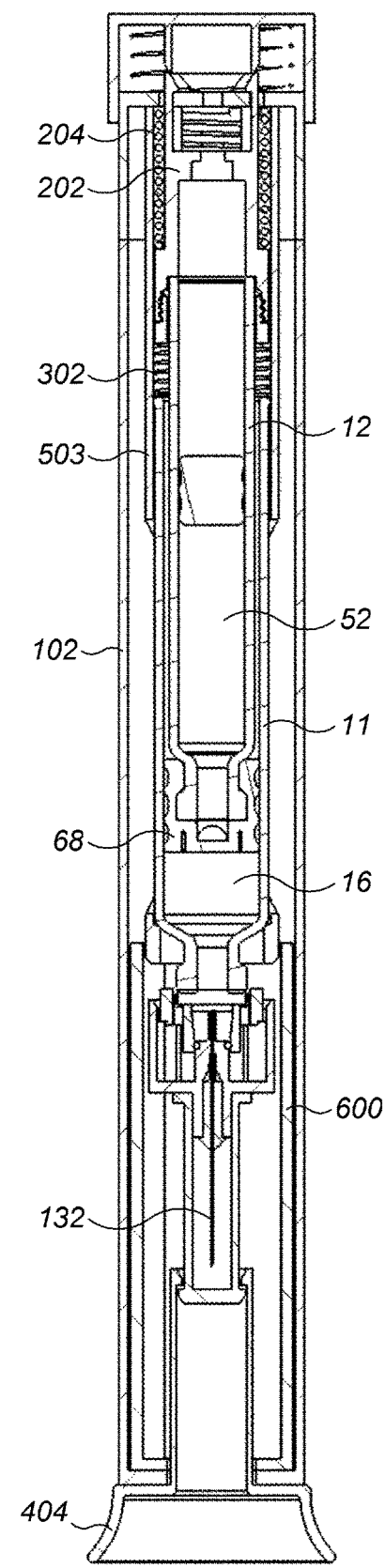
Figure 16A:
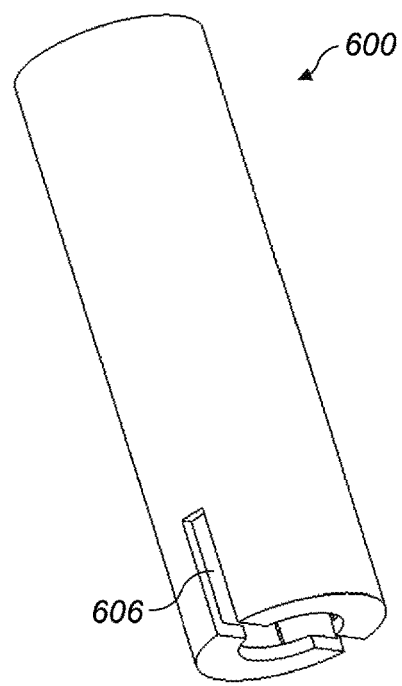
Figure 16B:
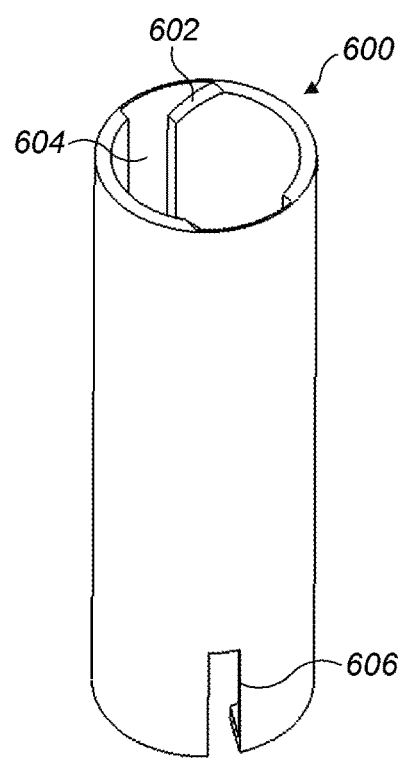
Figure 17:
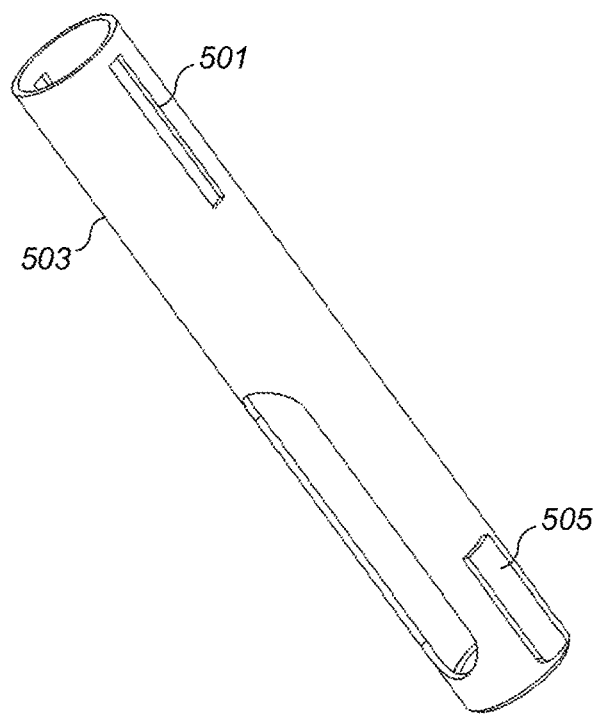

FIGS. 13(a), 13(b), 13(c), 13(d), and 13(e) are cross-sectional views of the device before and following operation of the trigger assembly;

FIGS. 14(a) and 14(b) show a second embodiment of the invention before and following the detachment of the container shroud respectively;

FIGS. 15(a) and 15(b) show cross-sectional views of a third embodiment of the invention through different planes;

FIGS. 16(a) and 16(b) show isometric views of the bottom and top of the release element of the third embodiment;

FIG. 17 shows an isometric view of the carriage of the third embodiment; and

Figure 18:
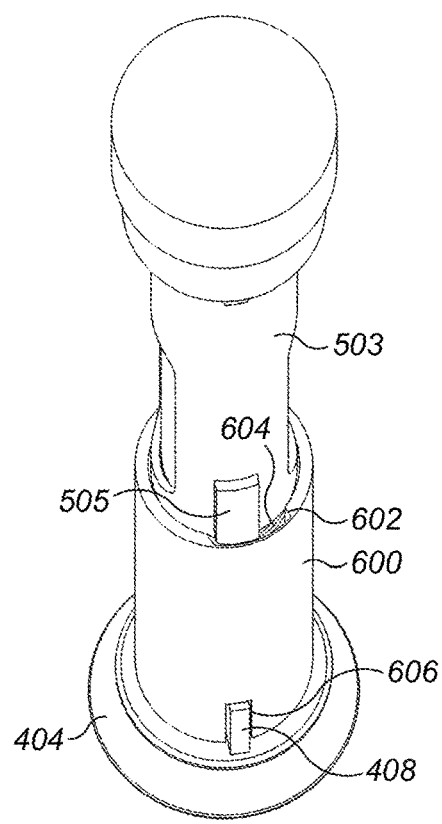

FIG. 18 shows an isometric view of the top of an assembled device according to the third embodiment, with the housing removed.

Figure 1:
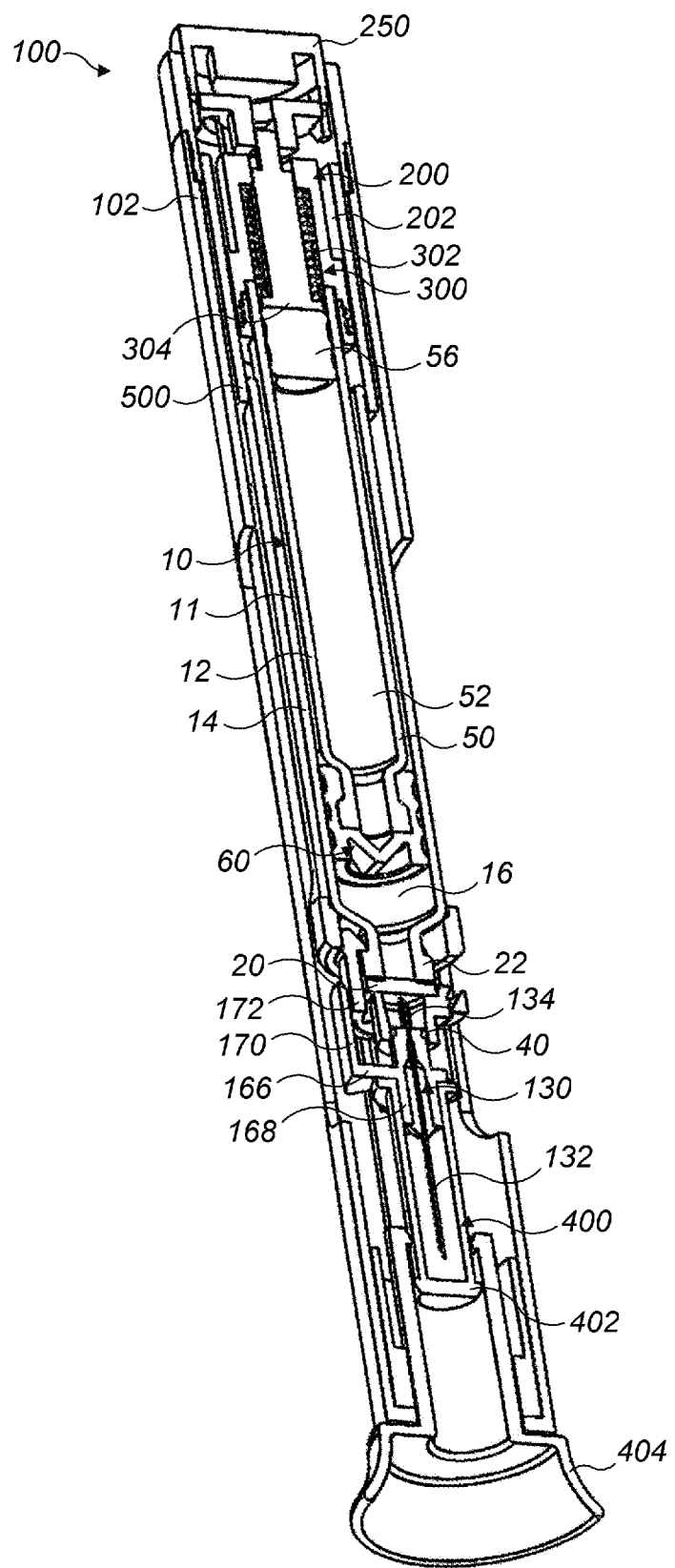
FIG. 1 is an isometric cross sectional view of a medicament delivery device according to a first embodiment of the present invention, when in an initial state.

Throughout this description, terms such as "top", "bottom", "upper" and "lower" are used with reference to the orientation of the devices as shown in FIGS. 1 and 13, although it will be understood that the device could be disposed in any suitable orientation in use, For convenience, the reference numerals used in the illustrative embodiments are summarised below:

| | |
|---|---|
| Cartridge-type medicament container | 10 |
| First container | 11 |
| Tubular body | 14 |
| First chamber | 16 |
| Outlet | 18 |
| Elastomeric disc or septum | 20 |
| Neck | 22 |
| Coupling element | 24 |
| Collar | 26 |
| Clip formations | 28 |
| Legs | 30 |
| Ring part | 32 |
| Tubular throat | 34 |
| Bore | 36 |
| Annular groove | 38 |
| Sealing ring | 40 |
| Second container | 12 |
| Tubular body | 50 |
| Second chamber | 52 |
| Neck | 54 |
| Stopper | 56 |
| Collar | 58 |
| Cap | 60 |

-continued

| | |
|---|---|
| Forward face | 62 |
| Annular ring part | 64 |
| Ridges | 66 |
| One-way slit valve | 68 |
| Wedge-shaped region | 70 |
| Valve members | 72 |
| Medicament delivery device | 100 |
| Housing | 102 |
| Bridge | 104 |
| Curved slots | 106 |
| Keying formation | 108 |
| Needle assembly | 130 |
| Hub | 166 |
| Central extension | 168 |
| Rearwardly-extending arms | 170 |
| Clip formations | 172 |
| Cannula | 132 |
| Internal piercing member | 134 |
| Drive mechanism | 200 |
| Drive element | 202 |
| Seat | 203 |
| Drive spring | 204 |
| Release slot | 205 |
| Latch formations | 206 |
| Central bore | 207 |
| Cam formations | 208 |
| Follower | 209 |
| Trigger assembly | 250 |
| Button | 252 |
| Delatching formation | 254 |
| Mixing mechanism | 300 |
| Mixing spring | 302 |
| Restraining pin | 303 |
| Mixing element | 304 |
| Release formation | 305 |
| Head | 306 |
| Cam formation | 308 |
| Needle shroud | 400 |
| Shroud body | 402 |
| Deshielder cap | 404 |
| Tubular projection | 406 |
| Link | 407 |
| Ribs | 408 |
| Pins | 409 |
| Chassis | 500 |
| Coupling | 501 |
| Control sleeve | 502 |
| Carriage | 503 |
| Chassis body | 504 |
| Bosses | 505 |
| Channel | 506 |
| Keying indents | 507 |
| Projecting fingers | 508 |
| Slots | 509 |
| Release element | 600 |
| Cam formations | 602 |
| Carriage tracks | 604 |
| Shroud tracks | 606 |

FIG. 1 shows a cross sectional view of a medicament delivery device 100 according to a first embodiment of the invention. The device 100 comprises a housing 102 that defines an elongate body that extends along a drive axis of the device 100 and houses a cartridge-type medicament container 10. A needle assembly 130 is disposed towards the bottom or distal end of the housing 102 and comprises a cannula or injection needle 132, which is enclosed by needle shroud 400. The needle shroud 400 comprises a shroud body 402, and deshielder cap 404 which projects from the distal end of the housing 102 and is connected to the shroud body 402 in slidable telescopic connection.

Remote to the cap 402, towards the top or proximal end, the housing 102 houses a drive mechanism 200, a trigger assembly 250, and a mixing mechanism 300. The drive mechanism 200 comprises a drive element 202 that may be actuated by trigger assembly 250 to be driven by a drive spring (not shown in FIG. 1) through a drive stroke to insert the cannula 132 and inject the medicament. Mixing mechanism 300 comprises a mixing element 304 that, upon release, is driven by mixing spring 302 through a mixing stroke to mix the reconstitutable medicaments contained in the cartridge 10.

Figure 2:
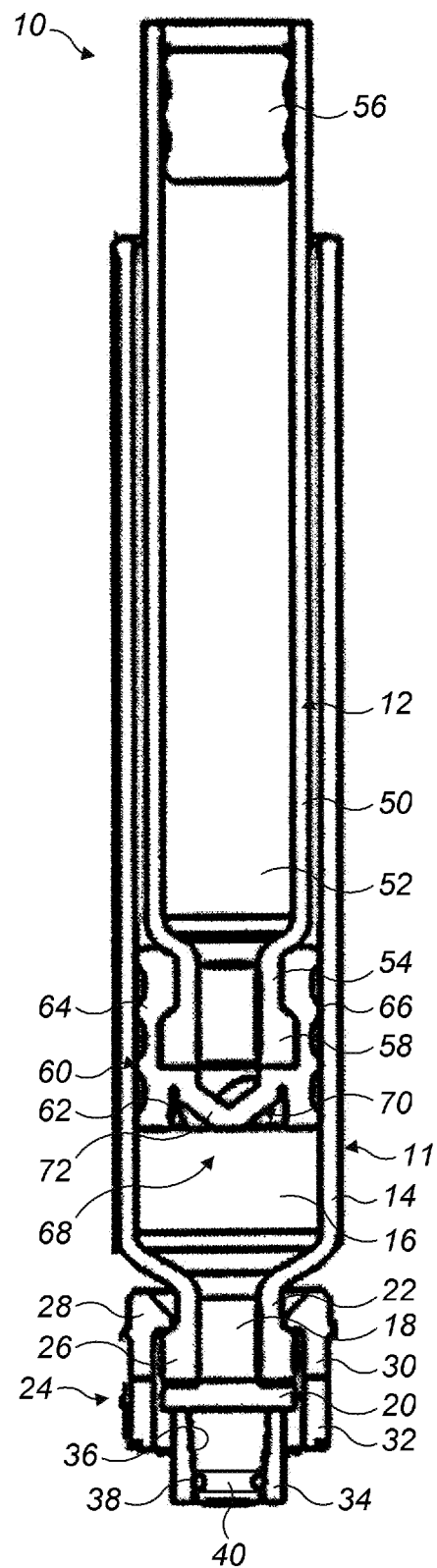
FIG. 2 is a cross-sectional view of the cartridge for use with the medicament delivery device of FIG. 1.

FIG. 2 shows the cartridge 10 in isolation. The cartridge 10 comprises a first or outer container 11 and a second or inner container 12 that is telescopably received in the rearward end of the outer container 11. The outer container 11 comprises a generally tubular body 14 that defines a first chamber 16 for containing a first substance. A first, distal end of the body 14 defines an outlet 18 of the first chamber 16 that is closed by a closure member in the form of an elastomeric disc or septum 20, which seals against the end face of a reduced-diameter neck 22 of the body 14.

The septum 20 is held in place by a coupling element 24 that is in clipped engagement with a collar 26 on the neck 22 of the body 14, by way of clip formations 28. The clip formations 28 are disposed at the ends of a plurality of legs 30 that extend proximally from a ring part 32 of the coupling element 24.

The ring part 32 supports a tubular throat 34 of the coupling element 24. The throat 34 is integrally formed with the coupling element 24, and defines a generally frustoconical bore 36. An inner end of the throat 34 presses against the septum 20 to seal the septum 20 against the end of the neck 22. The circumference of the throat 34 is uninterrupted so that a sealing force is applied to the septum 20 around a complete circle. An annular groove 38 for receiving a sealing ring 40 is disposed on the inside of the bore 36 adjacent to the distal end of the throat 34. The sealing ring 40 comprises an elastomeric O-ring. In this way, the sealing ring 40 may form a sterile seal around the hub 166 of needle assembly 130 and, together with a sealed needle shroud, may keep both ends of the cannula 132 sterile prior to use.

The proximal end of the first chamber 16 is closed by the inner container 12. The inner container 12 comprises a generally tubular body 50 that defines a second chamber 52 for containing a second substance. The inner container body 50 is similar in shape and construction to the outer container body 14, and thus comprises a neck 54 and a collar 58 that extends around the neck 54 at its distal end.

An elastomeric bung or stopper 56 is received in the outer container body 50 to close the proximal end of the second chamber 52. The distal end of the inner container body 50 is closed by a second or inner closure member in the form of a cap 60 that fits over the collar 58.

The cap 60 is formed from an elastomeric material, such as a halobutyl or other rubber material, and comprises a forward face 62 and an annular ring part 64 that extends rearwardly from the forward face 62 to receive the neck 54 of the inner container body 50. The ring part 64 is shaped to engage around and form a seal against the neck 54 on the rearward side of the collar 56 to secure the cap 60 to the inner container body 50. The cap 60 has an outer diameter that is sized so that a seal is formed between the cap 60 and the inner wall of the outer container body 14. To enhance the seal, a plurality of ridges 66 are formed on the outer surface of the cap 60.

The distal face 62 of the cap 60 is formed to provide a one-way slit valve 68 for closing the distal end of the second chamber 52. To this end, the distal face 62 comprises a generally wedge-shaped region 70 that faces distally away from the second chamber 52, and a slit extends through the cap 60 along the ridge to divide the wedge-shaped region 70 into a pair of valve members 72. The valve members 72 are biased towards one another so that, when fluid pressures on each side of the slit valve 68 are equal, the valve members 72 seal against one another to close the slit. When the pressure on the proximal side of the slit valve 68 is sufficiently greater than the pressure on the distal side, the bias of the valve members 72 can be overcome to allow fluid flow through the slit valve 68 in the distal direction. However, when the pressure on the distal side of the slit valve 68 exceeds the pressure on the proximal side, the valve 68 closes.

Turning back to FIG. 1, needle assembly 130 further comprises a hub 166 that forms part of a connection arrangement that is operable to establish a fluid connection between the first chamber 16 of the container 10 and the cannula 132. The hub 166 comprises a disc-shaped holder having a tubular, central extension 168 for holding cannula 132. Cannula 132 projects either side of the extension 168, with the upward projection towards the container 10 forming an internal piercing member 134. When the device 100 is in the initial state, the connection arrangement is in an unconnected configuration in which the hub 166 and the container 10 are arranged in a first attachment position relative to one another. In this first attachment position, the sealing ring 40 disposed on the inside of the bore 36 is retained by an annular groove on the outer face of the extension 168 of hub 166, and the piercing member 134 does not pierce the septum 20 so that the outlet 18 of the first container 11 remains closed. By virtue of the seal formed between the coupling element 22 and the extension 168 by the sealing ring 40, the piercing member 134 may be kept sterile in an enclosed chamber on the forward side of the septum 20. The hub 166 comprises a plurality of rearwardly-extending arms 170 that carry clip formations 172 that are engaged with the sides of the coupling element 24. During operation of the device, the coupling element 22 may slide downward relative to hub 166 such that the piercing member 134 pierces septum 20 for establishing the fluid connection between the first chamber 16 of the container 10 and the cannula 132.

Figure 3:
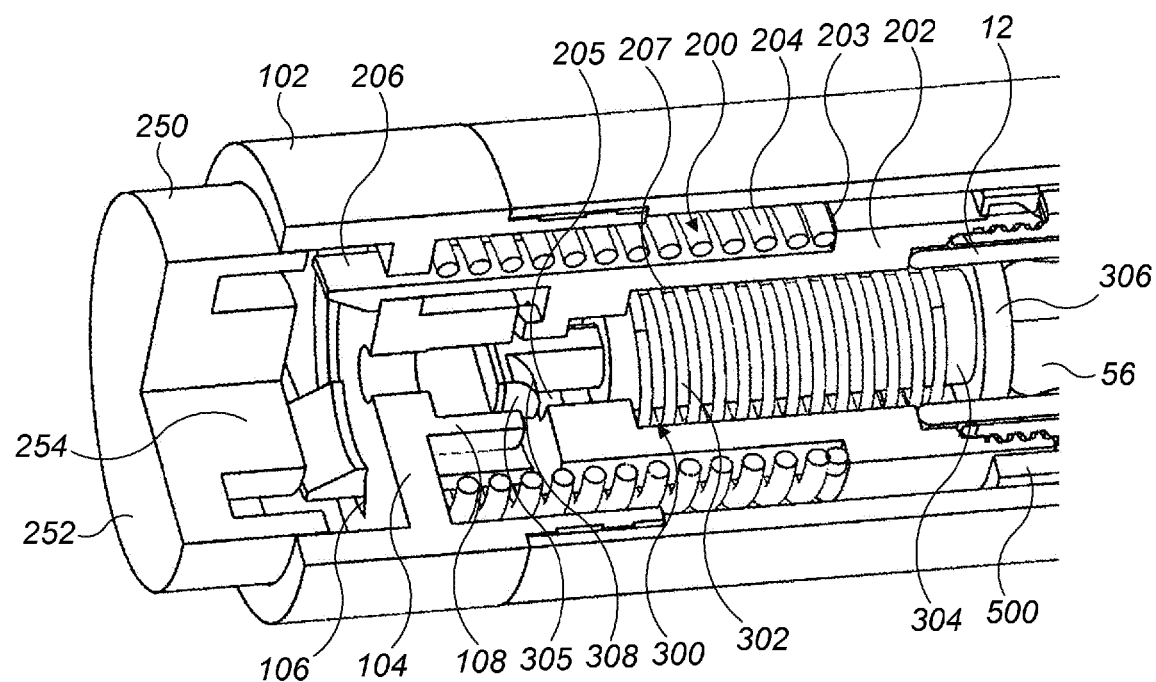
FIG. 3 is an isometric cut away view of the top of the delivery device of FIG. 1.
Figure 4:
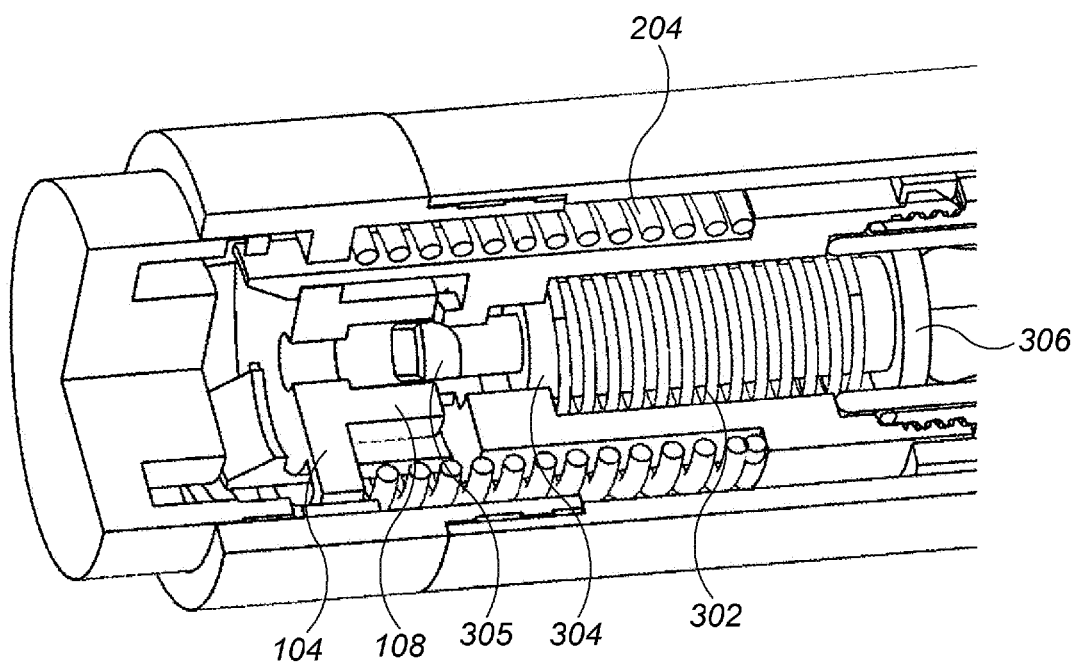
FIG. 4 is an isometric cut away view of the top of the delivery device of FIG. 1 once the drive element has rotated to its release position.

FIGS. 3 and 4 show a cut away view of the top or proximal end of the housing 102 of a medicament delivery device 100. As shown, the drive mechanism 200 comprises a drive spring 204 that, in its initial state, is compressed between a distal facing face of bridge 104 formed in the interior of housing 102 and an opposing seat 203 formed on the drive element 202. The drive element 202 is held in place by latch formations 206 that project upwards through curved slots 106 provided in the bridge 104 and are resiliently latched thereto. The curved slots 106 allow the drive element to be rotated axially with respect to the housing 102, whilst the latch formations 206 remain engaged to the bridge 106. Trigger assembly 250 comprises an actuatable button 252 which, when actuated, moves a delatching formation 254 downwardly for disengaging the latch formations 206 from their engagement with bridge 106, for thereby releasing the drive element 202.

The mixing mechanism 300 is fitted within a central bore 207 formed in drive element 202. The mixing spring 302 of mixing mechanism 300, in its initial state, is compressed between the roof of central bore 207 and a formation on the body of mixing element 304. The mixing element 304 is provided with an enlarged head 306 disposed at a distal end of its shaft that, upon activation, engages with stopper 56 of the second container 12 to move the stopper 56 distally relative to the second container 12 in a mixing stroke. The mixing element is retained in its initial state locked into the drive element 202 by a release formation 305 provided at the proximal end of the mixing element that extends proximally through a release slot 205 formed in the roof of the bore 207 of the drive element. The release formation 305 thereby provides a latching formation for latching the mixing element 304 to the release element 202.

Figure 6:
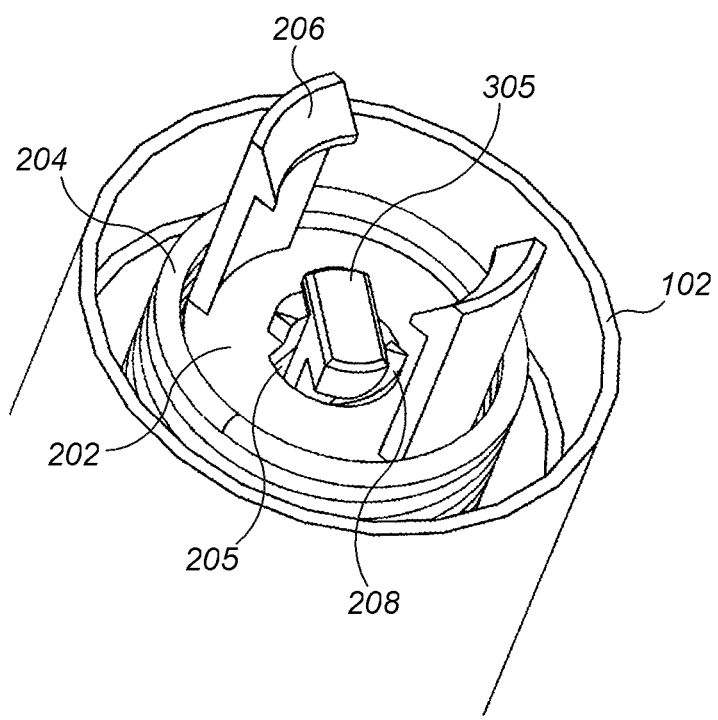
FIG. 6 is an isometric view of the top of the drive element and the release formation, with the trigger assembly omitted for clarity.

FIG. 6 shows a perspective view of the disassembled top of the device, with the trigger assembly 250 and the bridge 104 part of the housing removed. As shown, the release formation 305 extends upwards through the release slot 205 formed in the roof of the drive element 202. The release formation 305 and the release slot 205 are shaped such that the release formation can slide through release slot 205 when aligned. However, in its initial state, the release formation 305 is rotated relative to the slot 202 to form a mechanical lock for holding the mixing element in place. Cam formations 208 are provided on the proximal face of the roof of the drive element 202 and are engaged with cam formations 308 provided on the opposing distal face of the release formation 305. Consequently, under the bias load applied by the mixing spring 302, the caming action rotationally biases the drive element 202 to rotate relative to the mixing element 304 towards a position where the release formation 305 is aligned with slot 205 for releasing the mechanical lock. However, as discussed in more detail below, the drive element 202 prevented from rotating relative to the mixing element 304 in this initial state through its engagement with a chassis 500. As such, the drive element 202 functions as a release element that holds the mixing element 304 in place in an initial state, but is operable to rotate for releasing the mixing element.

Turning back to FIGS. 3 and 4, the bridge 104 formed in the interior of housing 102 is further provided with a keying formation 108 for receiving the head of the release formation 305 to rotationally lock the mixing member 304 to the housing 102. In this respect, FIG. 3 shows the release formation 305 in its initial state where it is axially locked to the drive element 202 with the release formation received into the keying formation. In FIG. 4, the drive element 202 has been released from its rotational lock to the housing 102, allowing it to rotate relative to the mixing member 304 under the bias provided by the engagement of cam formations 208 and 308. As such, in FIG. 4, the drive element 202 has rotated around the axis relative to the release formation 305, which remains rotationally locked to the housing 102 through its engagement with the keying formation 108. Once the drive element 202 has rotated, the release formation 305 is aligned with the release slot 205 for permitting the release formation to slide through and release mixing member 304.

Figure 5:
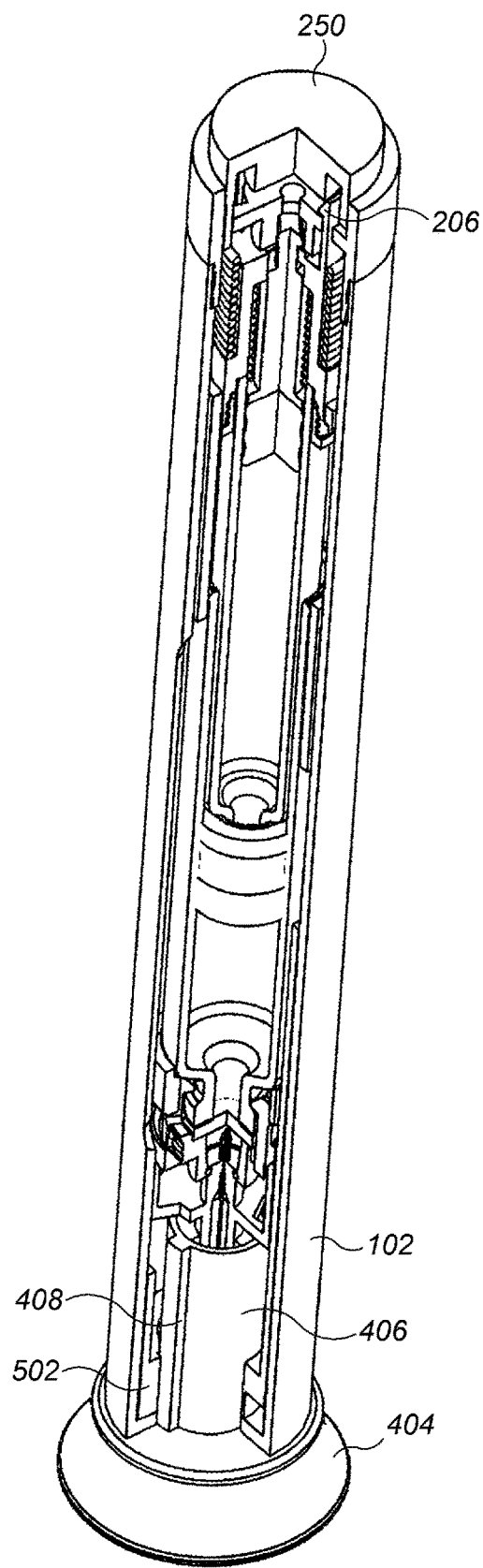
FIG. 5 is a cut away isometric view of the device of FIG. 1.

FIG. 5 shows a cut away view of the device when in its initial state. The cap 404 comprises a tubular projection 406 that is received into the distal end of the housing 102 and forms part of the slidable telescopic connection to the shroud body 402. The outer surface of the tubular projection 406 is provided with two ribs 408 which key into correspondingly shaped formations provided in the distal end of the housing 102 and in control sleeve 502 of the chassis 500. As such, when the cap 404 is received into the distal end of the housing 102, the ribs 408 function to rotationally lock the housing 102 and the chassis 500.

Figure 7:
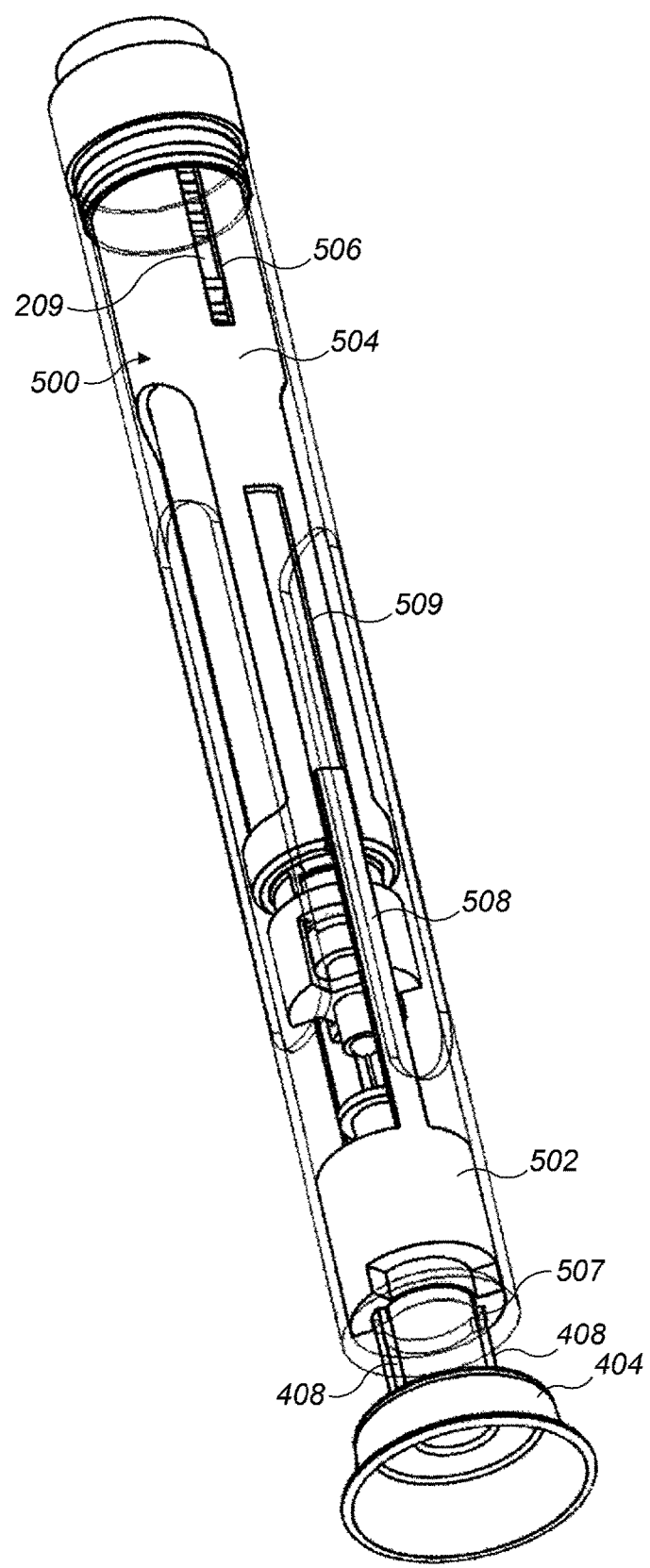
FIG. 7 is an isometric view of the device with the housing shown in wireframe to show the components of the chassis.

FIG. 7 shows a perspective view of the device with the housing shown transparent and the deshielder cap 404 partially detached. The chassis 500 comprises control sleeve 502 and chassis body 504. The control sleeve 502 has keying indents 507 that engage with ribs 408 at its distal end and projecting fingers 508 at its proximal end that rotationally lock into slots 509 provided on the chassis body 504, whilst allowing the chassis body 504 to move toward the control sleeve 502 when the device is actuated. The chassis body 504 further comprises an axially extending channel 506 for receiving a follower 209 provided on the drive element 202 and thereby rotationally locks the drive element 202 relative to the chassis 500.

The operation of the device will now be described in particular reference to FIGS. 8 to 13.

Figure 8:
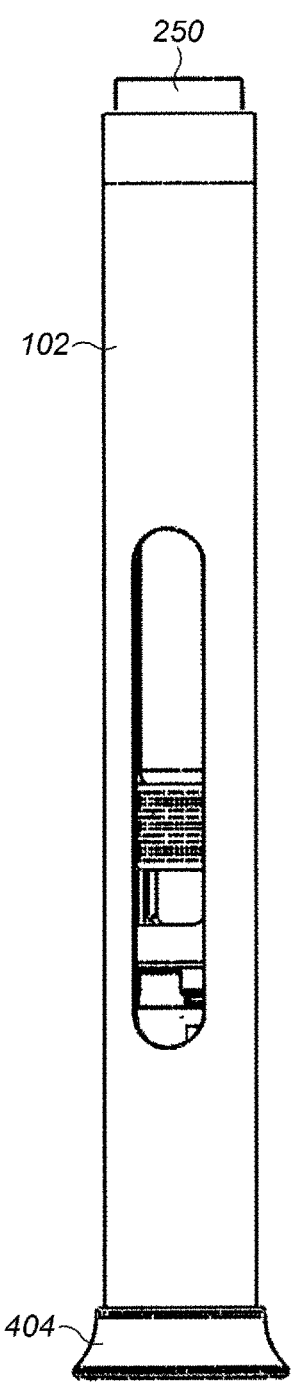
FIG. 8 is a side view of the device.
Figure 9:
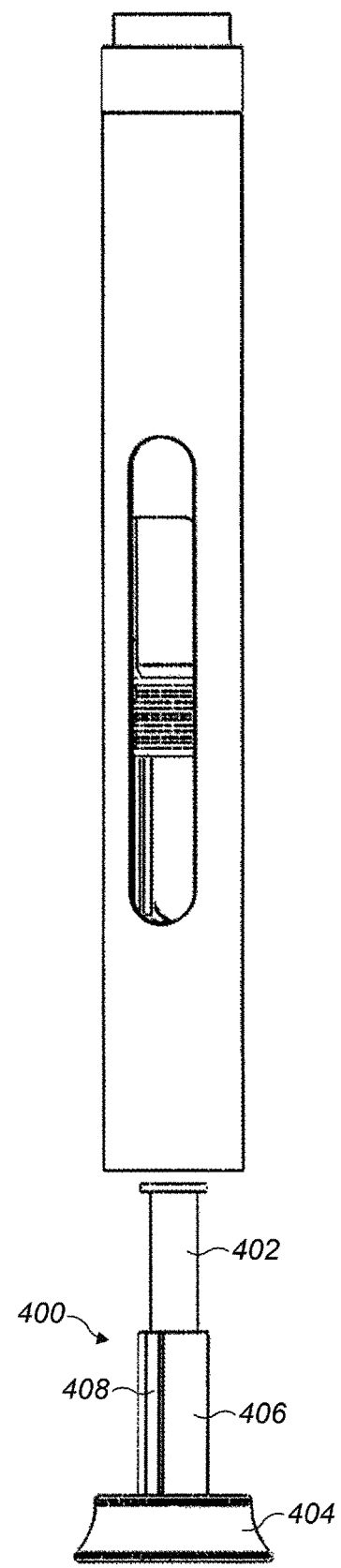
FIG. 9 is a side view of the device with the needle shroud removed.
Figure 10:
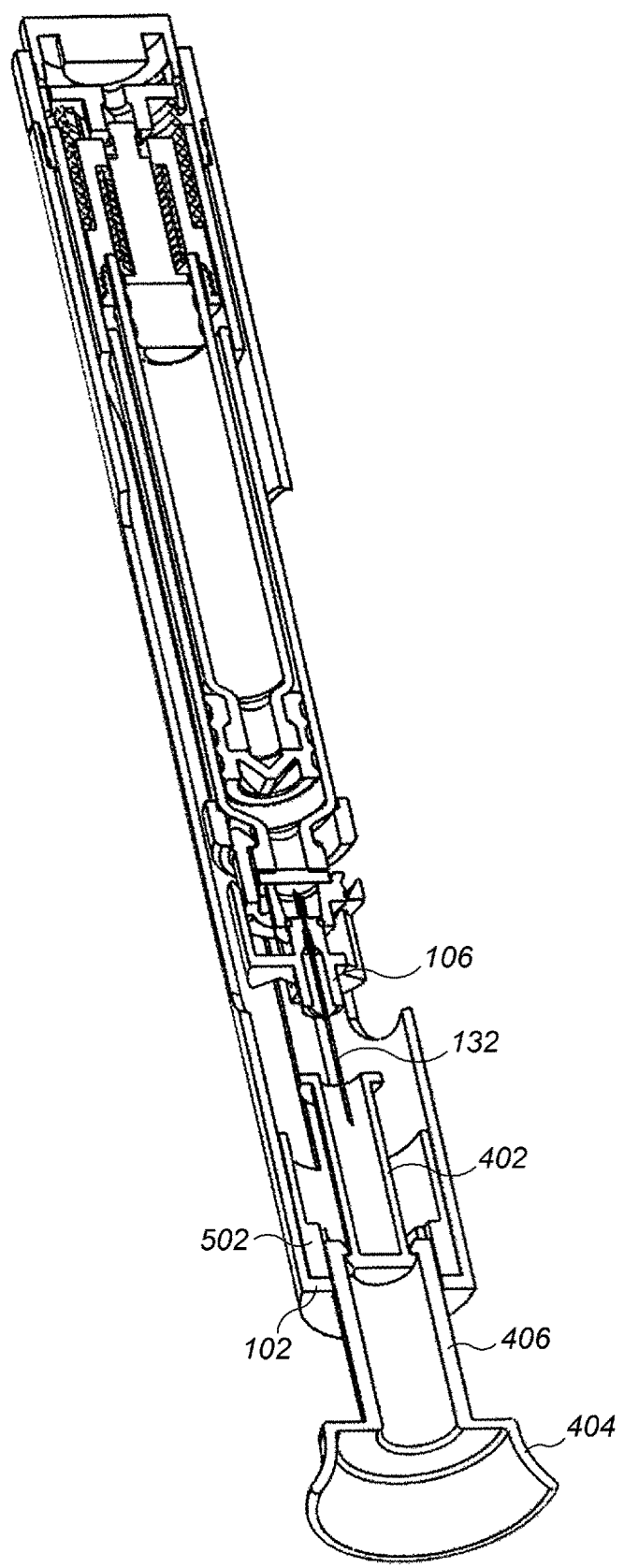
FIG. 10 is an isometric cross sectional view of the medicament delivery device of FIG. 1 with the needle shroud partially detached.

FIG. 8 shows a side view of the device 100 in its initial state, with housing 102 orientated so that the distal end of the device faces downwardly. To operate the device 100, the user first removes the needle shroud 400 by gripping the exposed cap 404 and pulling it out from the bottom end of the housing 102. As shown in FIG. 9, this draws out the tubular projection 406 from the housing, followed by the shroud body 402 once the slidable telescopic connection reaches its limit. In the interior of the housing, as shown in FIG. 10, this action detaches the shroud body 402 from the hub 166, thereby removing the sterile seal around the cannula 132 and leaving the cannula 132 unshrouded within the housing 102.

Figure 11:
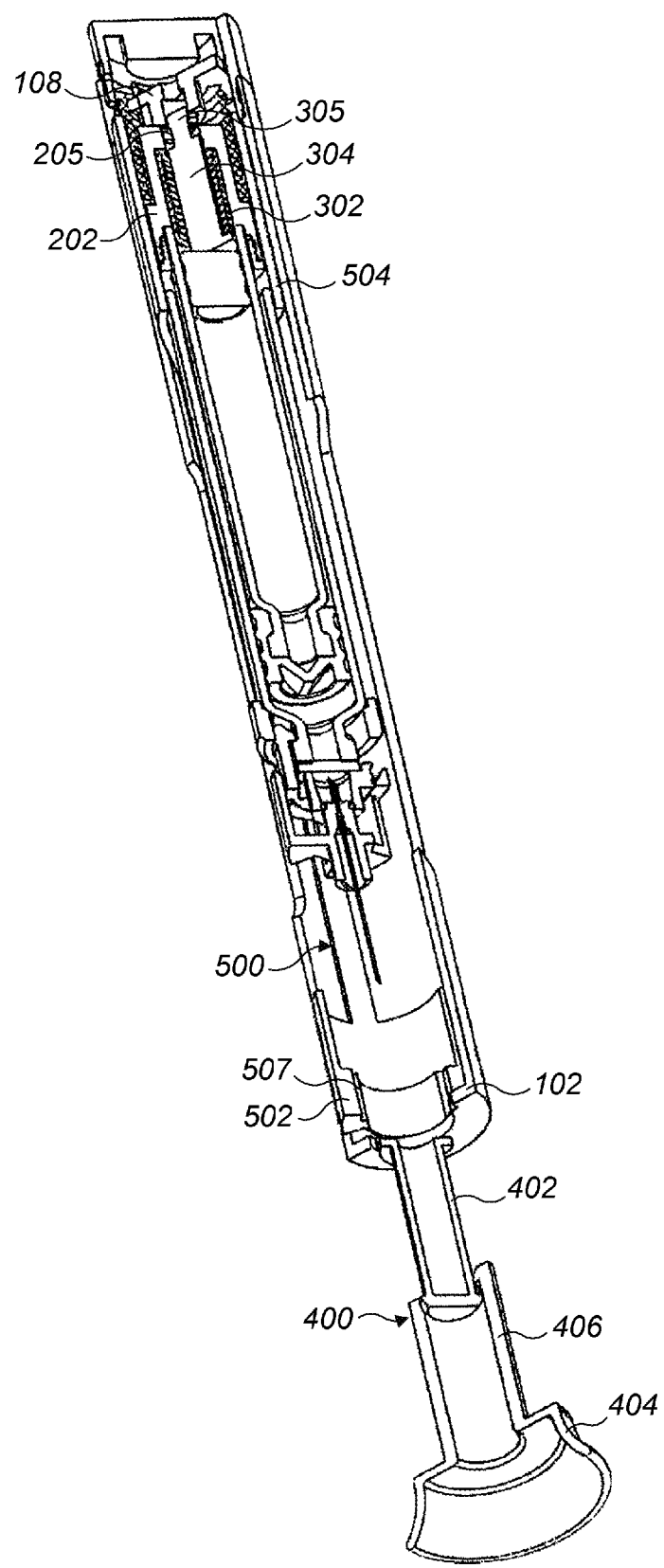
FIG. 11 is an isometric cross sectional view of the medicament delivery device of FIG. 1 with the needle shroud removed.

At the same time as the above, once the tubular projection 406 is removed from the device, the ribs 408 are disengaged from their engagement with the housing 102 and the keying indents 507 of control sleeve 502, which thereby allows the control sleeve 502 to rotate relative to the housing 102, as described above in relation to FIGS. 5 and 7. This release thereby allows the control sleeve 502 to rotate within the housing, as shown in FIG. 11, under the bias applied by the caming action described above in relation to FIGS. 3 and 4. That is, the release formation 305 of mixing element 304 is roationally locked to housing 102 through keying formation 108, but applies a rotational force to drive element 202 through the cam formations 208 and 308 to bias it to rotate. This force is transferred to the chassis body 504 that is rotationally locked to the drive element 202 through the slidable coupling of channel 506 and follower 209 shown in FIG. 7. In turn, the chassis body 502 transfers this rotational force through slots 509 to the projecting fingers 508 of control sleeve 502. As such, the chassis 500 and the drive element 202 rotates within the housing once the needle shroud 400 is removed.

Still in reference to FIG. 11, the rotation of the drive element 202 relative to the mixing member 304 further acts to align the release slot 205 with the release formation 305 of mixing element 304. This allows the release formation 305 to slide through the release slot 202 under the bias force applied in the distal direction to mixing element 204 by mixing spring 302. This releases mixing member 304, as shown in FIG. 12, allowing it to drive distally though a mixing stroke.

Figure 12:
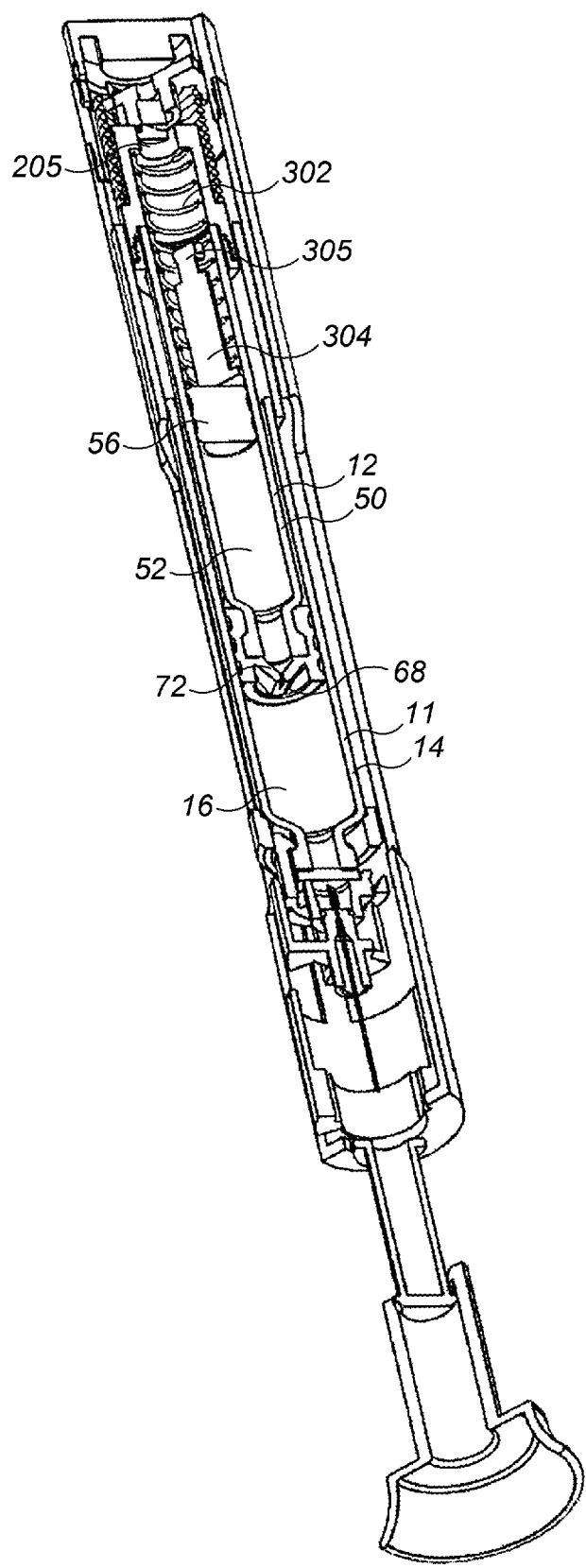
FIG. 12 is an isometric cross sectional view of the medicament delivery device of FIG. 1 after the mixing stroke has been initiated.

In this connection, as shown in FIG. 12, as mixing member 304 is moved in a distal direction under the influence of the mixing spring 302, the stopper 56 is displaced in the distal direction with respect to the second container body 50. The resulting pressure increase in the second chamber 12 causes valve members 72 of the slit valve 68 to open. Driven by the pressure increase, the second medicament substance flows from the second chamber 52 to the first chamber 16 to mix with the first medicament substance. The second container body 50 moves proximally with respect to the first container body 14 to conserve the total combined volume of the first and second chambers 52, 16.

Figure 13A:
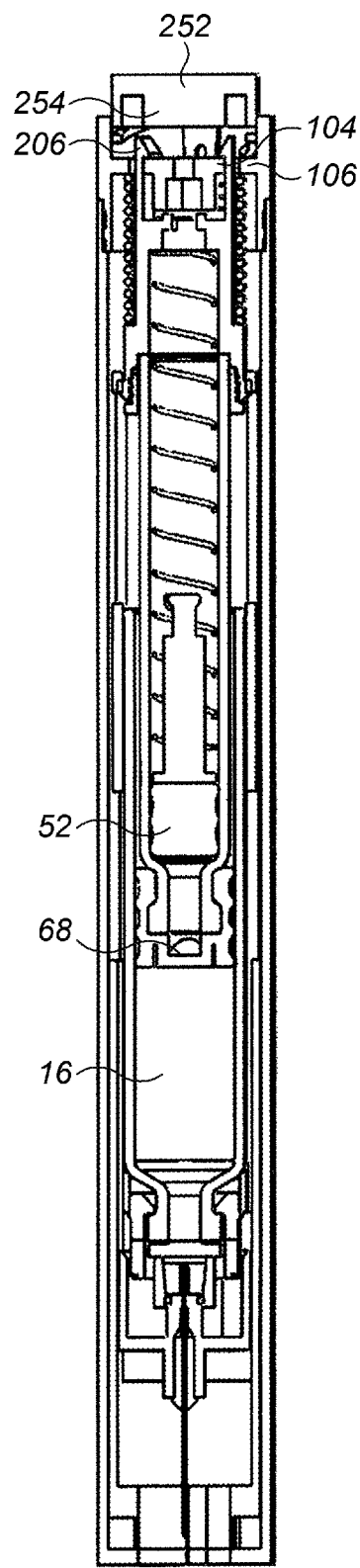

At the end of the mixing stroke, the slit valve closes 68, as shown in FIG. 13(a). The first chamber 16 now contains a mixture of the first and second medicament substances. Consequently, by the action of removing the needle shroud 400, a user initiates the mixing stroke and thereby reconstitutes the medicament.

Figure 13B:
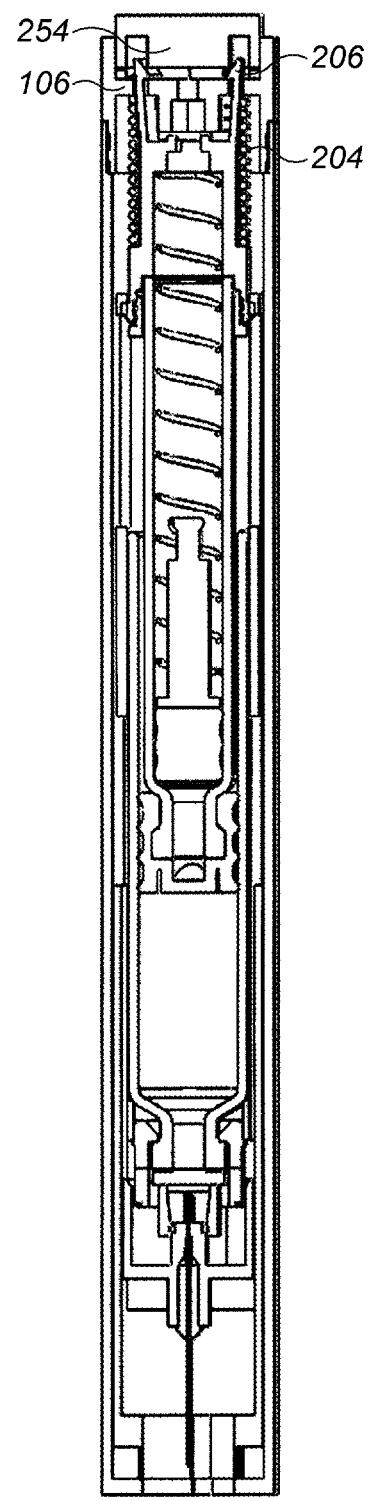

To perform an injection operation, the user may then locate the distal end of the housing at the injection site and press button 252 to move delatching formation 254 downwardly as shown in FIG. 13(b) to thereby disengage the latch formations 206 from their engagement with bridge 106.

Figure 13C:
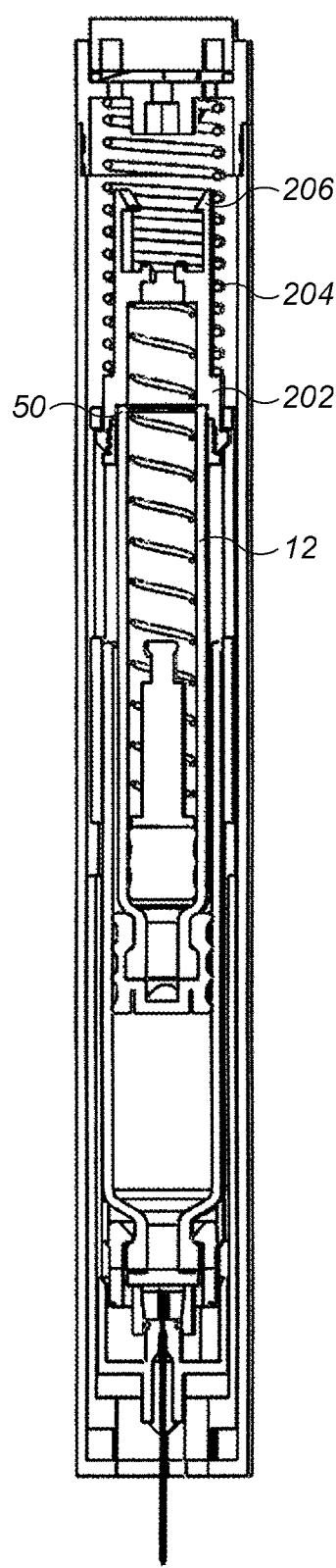

As shown in FIG. 13(c), this then releases the drive element 202 under the bias force applied in the distal direction by drive spring 204 to initiate the delivery stroke. The drive element 202 is engaged with the proximal end of the second container body 50 and thereby moves the second container 12 in the distal direction under the force applied by the drive spring 204. This increases the pressure on the distal side of the slit valve 68, thereby ensuring the valve 68 remains closed as the second container 12 advances. The integrity of the valve seal is re-enforced by the force bias applied to the mixing element. As shown, this movement advances the cannula 132 out of the distal end of housing 102 for insertion into the patient's skin.

Figure 13D:
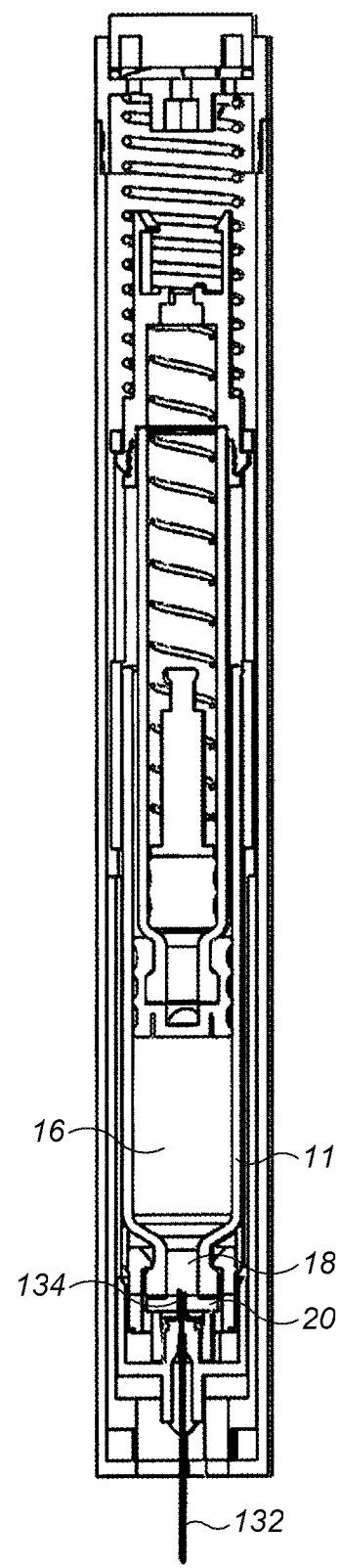

As shown in FIG. 13(d), as the cannula 132 moves into its inserted position, the second container 12 continues its advance in the distal direction and moves toward hub 166 so that the piercing member 134 part of the cannula 132 pierces the septum 20. This thereby connects the outlet 18 of the first container 11 to the cannula 132 for establishing a fluid connection for the medicament.

Figure 13E:
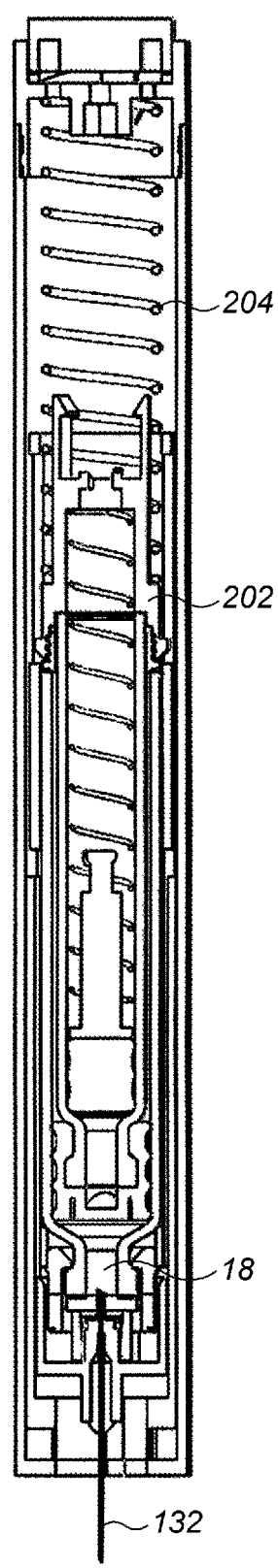

As shown in FIG. 13(e), as the second container 12 is driven further by drive spring 204, the volume of the first chamber 16 is reduced, thereby expressing the mixed medicament in the first chamber 16 through the cannula 132.

Once the delivery stroke is complete, the device 100 can be removed from the injection site and disposed of.

In summary, in an operating sequence of the device of the illustrative embodiment of the invention shown in FIGS. 1 to 13, the needle shroud 400 is first removed by the user which initiates the mixing of the first and second substances within the device. The device can then be positioned against the injection site, and the user can press the button 252. Movement of the button 252 first causes insertion of the cannula 132 into the user, then causes insertion of the cannula into the cartridge, and then delivery of the medicament.

Thus, with embodiments of the invention, the user operations required to operate the device for injection of a reconstitutable medicament are greatly simplified to the extent that they are comparable with auto-injector devices for non-reconstitutable medicaments. That is, conventional auto-injector devices for non-reconstitutable medicaments are often provided with a cap that is removed prior to use. With embodiments of the invention, however, the removal of the cap immediately initiates the medicament-mixing operation. The user may then initiate an injection operation simply by pressing a button to fire the drive mechanism in the way that they would with other auto-injector devices. This reduces the risk of mis-operation.

FIGS. 14(a) and 14(b) show an alternative second embodiment of the invention. In this embodiment, the deshielder cap 404 is formed as a container shroud that extends up around at least a portion of the housing 102 defining the body of the device. A resiliently flexible restraining pin 303 is provided that projects through a port in the housing 102 to restrain the mixing element in its initial position as in the first embodiment. The restraining pin 303 is coupled to the container shroud 404 by a link 407. In use, the container shroud 404 may be detached from the device, as shown in FIG. 14(b). FIG. 14(b) shows the container shroud 404 in wireframe for clarity. This removes the needle shroud body 402 from the housing for deshielding the cannula within the device. At the same time, the link 407 causes the restraining pin 303 to be pulled out of its port in the housing, thereby releasing the mixing element within the device to initiate the mixing stroke. As such, in use, removal of the container/needle shroud removes the restraining pin to initiate mixing.

Other mechanisms for mixing the first and second components of the reconstitutable medicament are also envisaged. For example, in the above illustrative embodiments, the mixing stroke is actuated by the mixing element engaging with the stopper to move it in the distal direction with respect to the first container. However, arrangements are also envisaged where, rather than moving a stopper, the mixing element moves the first or second containers relative to the other to create a reduced or negative pressure in the first container. In such embodiments, the mixing element may be a spring biased to act on one of the first or second containers. For example, the mixing element may be engaged with the second container and be biased in the proximal direction. As such, when the mixing element is released, it moves the second container rearward in the proximal direction with respect to the first container. This causes a drop in pressure in the first chamber, which thereby opens the valve between the chambers and drives flow of the second substance from the second chamber into the first chamber. Under the influence of this negative pressure, the stopper would move in the distal direction with respect to the second container during the mixing stroke as the volume of the second chamber decreases and the volume of the first chamber increases. A vent may be provided in the mixing element to admit air to the second container on a proximal side of the stopper to allow free movement of the stopper. Furthermore, embodiments are also envisaged where the mixing element is engaged with the first container and the second container is initially held in place relative to the housing. On removal of the needle shroud, the mixing element is released and the first container is sprung forwards in the distal direction to increase its relative volume as it moves away from the second container. This generates a negative pressure in the first container for displacing the second substance into it. The device may then be fired by releasing the second container relative to the housing under action of a drive spring.

In this connection, FIGS. 15 to 18 show a third embodiment of the invention which utilises the above described negative pressure mixing mechanism. Like numbered reference numerals to those used in the previous embodiments have been used for corresponding features. FIGS. 15(a) and 15(b) show cross-sectional views of the third embodiment through different planes when the device is in its initial state. In this embodiment, the second container 12 is fixed to the drive element 202, which in turn is releasably latched to the top of the housing 102 against drive spring 204, but can be released by delatching formations 254 on button 252 when the device is fired. The first container 11 is connected to movable carriage 503, which is shown in more detail in FIG. 17, and is biassed downward in a distal direction by mixing spring 302 as shown in FIGS. 15(a) and 15(b). As shown in FIG. 17, the outer surface of the moveable carriage 503 is provided with two bosses 505 that, in response to the needle shroud 400 being removed, can key into and slide down carriage tracks 604 formed in release element 600, as shown in FIG. 16(b) and described in further detail below.

FIGS. 16(a) and 16(b) shows isometric views of the bottom and top of the release element 600 of the third embodiment. The release element 600 defines a rotatable ring and comprises a bore formed with carriage tracks 604 for receiving the bosses 505 of carriage 503 when aligned. The proximal ends of the carriage tracks comprise cam formations 602 which engage with the distal ends of bosses 505 of the carriage 503 when the release element 600 is in an initial locked position, as shown in FIG. 18. As such, the carriage 503 is prevented from moving distally down under the bias of the mixing spring 302. That said, the distal bias applied by mixing spring 302 acts through the cam formations 602 to bias the release element 600 to rotate towards an aligned position for guiding the bosses 505 into the carriage tracks 604. To resist this bias, shroud tracks 606 are provided at the distal end of the release element for receiving the ribs 408 of the needle shroud 400, as shown in FIG. 18 which provides an isometric view of the top of an assembled device with the housing removed.

In this connection, in the device's initial position, where the needle shroud 400 is engaged with the housing, the ribs 408 of the needle shroud 400 are keyed into keying formations provided in the distal end of the housing 102 to rotationally lock the needle shroud 400. The release element 600 is thereby prevented from rotating out of its locked position by the ribs 408 of the needle shroud 400 keying into both shroud tracks 606 of the release element 600 and the keying formations of the housing 102. In this position, the release element 600 prevents the carriage 503 from moving distally under the bias of the mixing spring.

When the needle shroud 400 is removed by a user by pulling out deshielder cap 404, the ribs 408 are withdrawn from their engagement with the keying formations in the distal end of the housing and the shroud tracks 606 of the release element 600. This thereby allows the release element 600 to rotate within the housing 102. As such, the release element 600 rotates to align the carriage tracks 604 with bosses 505 under the distal bias applied by the mixing spring 302 acting on carriage 503 and applying a distal force to cam formations 602. This rotation of the release element 600 allows the bosses 505 to move down into tracks 604, thereby releasing the carriage 503 and allowing it to move distally down under the bias applied by the mixing spring 302. As the first container 11 moves with the carriage 503, the volume of the first chamber 16 expands, with the corresponding drop in pressure drawing the second substance from the second container 12 into the first through the valve 68 to mix the constituents. That is, the negative pressure acts to displace the second substance from the second chamber 52 into the first chamber 16 to initiate mixing. The length of the mixing stroke may be determined by the limits of a slidable coupling 501 provided in the side of the carriage 503, as shown in FIG. 17, which is engaged with a follower formed on the drive element 202. Once the mixing stroke has completed, the button 252 can be pressed by a user to delatch the drive element 202, thereby allowing it to move distally down, along with the second container 12, under the bias applied by drive spring 204 to thereby expel the reconstituted medicament from the first container 11 through the cannula 132.

The third embodiment advantageously offers a relatively simple mechanism and construction because the release/latching mechanism for holding the first container in its initial position may be located towards the front of the device, thereby eliminating the need to rotationally link selective components through the length of the device.

It will be understood that the embodiments illustrated above shows applications of the invention only for the purposes of illustration. In practice the invention may be applied to many different configurations, the detailed embodiments being straightforward for those skilled in the art to implement.

In this connection, for example, it will also be understood that actuation of the button to release the drive element and initiate the injection operation may be restrained until the mixing element has been released.

It will also be understood that in the above illustrative first embodiment, cam formations are used to translate the axial bias of the mixing spring on the mixing element into a rotational bias acting on the drive element which functions as the release element.

However, it will be understood that other arrangements are also possible. For example, the release element could be rotationally biased to its release position by using a combined torsion and compression spring as the drive spring. Consequently, in such an arrangement, the drive spring would function to both rotationally bias the release element to release the mixing element and, later in the operation sequence, drive the release element as a drive element for performing the delivery stroke.

Devices according to the invention may also include additional features as are generally known in the field. For example, to prevent contact with the needle after removal of the device from the injection site, a device according to the invention may include a deployable shroud arrangement that is disposed around the needle and that extends downwards to conceal the needle upon removal of the device. Alternatively, a mechanism for retracting the needle from the injection site automatically to shroud the needle in the housing after delivery of the medicament may be provided. It will also be appreciated that alternative drive mechanisms and trigger assemblies suitable for use in devices of the invention will also be known to those of skill in the art. Furthermore, a safety interlock mechanism may also be provided for preventing the device from being fired until it is placed against an injection site. Such safety interlock mechanisms are known to those of skill in the art and would typically include an unlocking member that extends from the front of the device and releases the trigger assembly when it is depressed against a patient's skin once positioned at the injection site.

It is also conceivable that various features included in the above-described example could be omitted. For example, for some applications, the connection arrangement may be omitted, in which case a fluid connection between the outlet of the cartridge and the needle may be established during assembly of the device.

In place of a hypodermic needle, devices according to the invention may comprise an alternative cannula, such as a flexible cannula, or may be adapted for use with such a cannula, an infusion set, or other suitable delivery means. In such cases, the above-described mechanisms for inserting the needle into the injection site may be modified (for example to facilitate automatic fluid connection to a cannula) or omitted.

Devices according to the invention may be used with cartridges that differ from the example described above, and the hub may cooperate with the cartridge to open the outlet and establish fluid communication in any suitable way. For example, in place of a pierceable septum, alternative means for sealing the outlet of the chamber may be provided, such as a releasable valve. The hub may therefore include a sealing element release member for cooperation with the sealing element to open the outlet.

It will be appreciated that the operational sequence of the devices could differ from the specific examples described above. For example, movement of the hub to establish fluid communication between the container and the cannula or injection needle could occur before or after insertion of the injection needle to the injection site.

It will further be understood that, in the context of this specification, the term "mixture" is used to refer to any chemical or physical combination of two or more starting substances, and references to "mixing", "mixed" and related terms should be construed accordingly. Thus "mixing" should be taken to include the formation of a solution, suspension, emulsion, colloid, gel, sol, foam, and so on. The term "mixing" also includes the bringing together of two or more reactants that react together upon mixing to form a new chemical compound.

Further modifications and variations of the above-described examples are also possible without departing from the scope of the present invention as defined by the appended claims.

The invention claimed is:

1. A medicament delivery device for delivery of medicament through a cannula from a cartridge comprising a first container for storage of a first substance, a second container for storage of a second substance and being arranged coaxially with respect to the first container, and a valve for closing a distal end of the second container, the medicament delivery device comprising:
   a mixing element comprising a stopper for causing displacement of the second substance into the first container through the valve in a mixing stroke;
   a release element comprising a cam formation for holding the mixing element in an initial position and operable to release the mixing element to initiate the mixing stroke; and
   a needle shroud for shrouding the cannula within an interior of the housing,
   wherein removal of the needle shroud from the interior of the housing causes operation of the release element.

2. The medicament delivery device according to claim 1, wherein the mixing element further comprises a spring.

3. The medicament delivery device according to claim 1, wherein the first container is moved in a distal direction with respect to the second container in the mixing stroke for displacing the second substance into the first container.

4. The medicament delivery device according to claim 3, further comprising a housing for receiving the cartridge, and wherein the second container is restrained relative to the housing during the mixing stroke.

5. The medicament delivery device according to claim 1, wherein the first container is biased in a distal direction by the mixing element and the release element restrains the first container in an initial position against the distal bias.

6. The medicament delivery device according to claim 1, wherein the stopper is driven by a mixing spring in the mixing stroke.

7. The medicament delivery device according to claim 1, wherein the mixing element further comprises a latch formation for engagement with the release element when in the initial position.

8. The medicament delivery device according to claim 7, wherein the release element is moveable relative to the latch formation for releasing the mixing element.

9. The medicament delivery device according to claim 8, wherein operation of the release element comprises rotational movement for aligning a slot provided in the release element with the latch formation to release the mixing element.

10. The medicament delivery device according to claim 1, further comprising a housing for receiving the cartridge and a chassis rotatable within the housing to initiate the mixing stroke upon removal of the needle shroud from the cannula.

11. The medicament delivery device according to claim 10, wherein the housing comprises a keying formation for engagement with the mixing element to rotationally lock the mixing element relative to the housing when in its initial position.

12. The medicament delivery device according to claim 10, wherein the chassis comprises a chassis body and a control sleeve rotationally locked to the chassis body and axially moveable relative thereto.

13. The medicament delivery device according to claim 10, wherein the needle shroud engages with the housing and the chassis when shrouding the cannula for preventing relative rotation therebetween.

14. The medicament delivery device according to claim 13, wherein the needle shroud comprises keying formations for engagement with the housing and the chassis for preventing relative rotation.

15. The medicament delivery device according to claim 6, wherein the chassis is rotationally locked to the release element.

16. The medicament delivery device according to claim 1, wherein the release element is biased for rotation to release the mixing element.

17. The medicament delivery device according to claim 16,
wherein the mixing element comprises a latch formation for engagement with the release element when in the initial position; and
wherein the latch formation engages with the release element at a cam surface for biasing the release element to rotate to release the mixing element.

18. The medicament delivery device according to claim 17,
wherein the mixing element comprises a stopper for being driven by a mixing spring in the mixing stroke; and
wherein a bias of the mixing spring on the mixing element in a distal direction applies the rotational bias to the release element through the cam surface.

19. The medicament delivery device according to claim 1, wherein the needle shroud comprises a cap projecting from a distal end of the device for facilitating removal of the needle shroud by a user.

20. The medicament delivery device according to claim 1, wherein release element is further moveable in a distal direction to cause movement of the second container in the distal direction to displace a mixture of the first and second substances through the cannula in a delivery stroke of the device.

21. The medicament delivery device according to claim 1, further comprising a needle assembly supporting the cannula, the needle assembly comprising a sealing ring for forming a sterile seal around a coupling between the first container and a proximal end of the cannula.

22. The medicament delivery device according to claim 1, wherein the needle shroud comprises a sealing ring for forming a sterile seal around a distal end of the cannula.

23. A combination of the device according to claim 1 and a cartridge.

24. A medicament disposed in the delivery device according to claim 1.

25. A method of treating a patient having a condition susceptible to treatment with a medicament, the method comprising: dispensing an effective amount of the medicament to the patient utilizing the delivery device according to claim 1.

* * * * *